United States Patent
Peterson

[11] Patent Number: 6,038,934
[45] Date of Patent: Mar. 21, 2000

[54] SAMPLER APPARATUS AND METHOD OF USE

[76] Inventor: Roger Peterson, Drawer 567 County Rd. 375, Old Ocean, Tex. 77463

[21] Appl. No.: 08/347,900

[22] Filed: Dec. 1, 1994

Related U.S. Application Data

[63] Continuation of application No. 08/116,716, Sep. 3, 1993, abandoned, which is a continuation-in-part of application No. 07/882,033, Jul. 13, 1992, Pat. No. 5,345,828, which is a continuation-in-part of application No. 07/895,788, Jun. 9, 1992, Pat. No. 5,279,167, which is a continuation-in-part of application No. 07/978,622, Nov. 19, 1992, Pat. No. 5,396,812.

[51] Int. Cl.$^7$ .............................. G01N 1/00; G01N 31/00
[52] U.S. Cl. ........................................... 73/863.86
[58] Field of Search ................ 73/23.42, 863.25, 73/863.81, 863.83, 863.85, 863.86, 864.14, 864.34, 864.74

[56] References Cited

U.S. PATENT DOCUMENTS

| | | | |
|---|---|---|---|
| 3,372,573 | 3/1968 | Sanford et al. | 73/23.1 |
| 4,572,780 | 2/1986 | Owen et al. | 422/145 |
| 4,689,206 | 8/1987 | Owen et al. | 422/144 |
| 4,791,821 | 12/1988 | Spencer | 73/864.74 |
| 4,879,915 | 11/1989 | Spencer | 73/864.74 |
| 4,962,042 | 10/1990 | Morabito et al. | 436/161 |
| 4,986,138 | 1/1991 | Spencer | 73/864.34 |
| 5,003,830 | 4/1991 | Spencer | 73/863.83 |
| 5,220,513 | 6/1993 | Seiden et al. | 73/19.01 |
| 5,325,823 | 7/1994 | Garcia-Mallol | 122/4 D |

FOREIGN PATENT DOCUMENTS

| | | | |
|---|---|---|---|
| 2343239 | 9/1977 | France | 73/863.83 |
| 0725235 | 9/1942 | Germany | 73/863.83 |
| 2918768 | 11/1980 | Germany | 73/863.83 |
| 0868429 | 9/1981 | U.S.S.R. | 73/863.83 |

*Primary Examiner*—George Dombroske
*Attorney, Agent, or Firm*—Gunn & Associates, P.C.

[57] ABSTRACT

This disclosure is directed to a system for providing a sample. It incorporates and appropriately connected valve element working with a surrounding seat and housing. The valve element responds to pressure from the atmosphere which purges the valve element of remnants of a sample passing therethrough so that no trace constituents are left in the valve element. The valve element is a two position, three way valve element which is rotated, thereby permitting a purge gas to flow or not flow, and it rotated to another position permitting the sample of interest to flow or not flow. A sequence of operations is defined.

9 Claims, 1 Drawing Sheet

SAMPLER APPARATUS AND METHOD OF USE

The present application is a continuation of Ser. No. 08/116,716 filed Sep. 3, 1993 now abandoned and continuation in part of Ser. No. 07/882,033 filed Jul. 13, 1992 now U.S. Pat. No. 5,345,828 continuation in part of Ser. No. 07/895,788 filed Jun. 9, 1992 now U.S. Pat. No. 5,279,167, and continuation in part of 07/978,622 filed Nov. 19, 1992, now U.S. Pat. No. 5,396,812.

The present disclosure is directed to both a method and apparatus for taking samples. More importantly, it is concerned with obtaining a bottled sample from an onstream sample monitoring apparatus which constantly monitors the production of a manufacturing process or the like. Consider as an example a petrochemical plant which operates for months, perhaps even for a year between periodical shut downs. During the time of its operation, the products which are made by the plant are constantly monitored to check product quality. For instance, the sales price of the product may depend on the nature or the amount of ingredient purity. Thus, the price of the product which is made by the process may be reduced if there are excessive impurities in it. The entire production of the plant may be sold at a price per pound or per cubic foot which varies as a function of product purity. If the process makes impure product, the price which it commands in the market may be reduced dependent on the extent or nature of the impurities in it. This typically requires repetitive sampling. A sample is periodically collected and taken to a test laboratory or other assay facility so that the sample can then be tested. While the sample may be small, the economic impact of the sample can be very substantial, for instance, in the situation where the plant makes thousands of pounds of product per hour and samples are only collected four times per day.

It is highly desirable that the sample be as representative as possible. One mode of assuring that the sample is representative of the product which is manufactured by the process involves periodic sampling with a sample collected and removed in a measured container. To accomplish this, the sample container must be filled by the sampling apparatus.

As disclosed in the foregoing patent applications, it is very important to collect these samples with a minimum escape of fumes to atmosphere. Practically every product forms a volatile discharge to atmosphere. This is commonly the fact with petrochemical plants which manufacture volatile constituents. This is true whether the discharge is liquid or gas. As shown in the foregoing disclosures, an apparatus and method are set forth which enable the capture of a sample in a purged sample container. This container, whether made of plastic or glass, is typically small, typically sized so that it holds a standard measure such as one or two liters. Moreover, the sample container is closed at the top where the container is constructed with a narrow neck and the narrow neck is sealed by a septa. The septa is punctured by narrow gauge needles which permit the introduction of sample into the jar. The present disclosure sets forth a procedure whereby the sample container can be installed in the system and initially purged with an inert gas. The inert gas is delivered by one syringe needle into the sample container and flows out of the sample container through another syringe needle. This assures that the initial status of the sample container is always the same from sample to sample. This further assures that the sample stored in the container is confined with an inert atmosphere. When the container has been adequately charged with the desired sample, it is then disconnected from the apparatus and is removed to a laboratory for testing. This involves the removal of the sample container, particularly disengaging the sample container from the two syringe needles of the present apparatus. As noted in the foregoing disclosures, one of the needles is utilized to deliver the sample into the container and the other needle is utilized to provide an outlet pathway for displaced inert gas. Also, if overfilling occurs, as may be the case, any surplus of the sample is delivered through the second needle. It is not discharged to atmosphere; rather, it is discharged through a filter system so that the filter system is able to prevent unintended discharges to atmosphere.

The present apparatus and method set forth a system so that flow spaces in the sample collecting apparatus are purged. The purging of the flow spaces precedes the delivery of sample through a control valve. In this instance, the control valve has fluid flow spaces which extend from the process to the sample collection container. These pathways risk commingling the sample with the atmosphere in the pathways. This system prevents such accidental mixing by clearing these pathways or flow paths through the structure so that the process sample delivered through the flow paths is appropriately purged in timely fashion.

Another important factor of the present disclosure is the ability of the system to operate continuously with a sample container first being installed, then filled and removed; then another sample container is installed in the equipment. The process continues indefinitely without the risk of discharge of the volatile sample material to atmosphere. It is particularly useful for a permanent installation so that the sample container does not discharge when being plugged into the apparatus and when being removed for subsequent transportation to the laboratory.

The present method is summarized as a multiple step sequence utilizing a control valve to connect the sample collection bottle of the present disclosure with a process plant. This valve has two positions, one of which connects the process plant flow to the sample container and the other which blocks flow from the plant. There is, however, a pilot passage formed in the valve element so that it serves as a two position, three way valve element. The smaller pilot passage is incorporated so that purge gas can be introduced. The purge gas is delivered to the system through a purge control valve. This provides an off and on function. When the process is not in operation, the purge valve can be closed to prevent wasting purge gas. More importantly, the valve controls flow so that sample does not escapte to atmosphere when the bottle is removed and the needles are exposed to the atmosphere. When the purge valve is open, the main valve is then provided with the purge gas when it is switched to the appropriate position. The two position, three way valve enables gas flow to first purge the sample bottle and the flow lines through the valve apparatus. The next position interrupts the purge gas flow. Rather, it provides process sample through the flow pathways in the valve mechanism and fills the sample bottle with the sample material in question. Any surplus will overflow through a filter system. The third position restores the main valve to the initial position which blocks flow from the process and yet which permits flow of the purge gas. This can then be used to purge the sample valve. The fourth position permits the purge gas to be switched off.

DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 1 is a schematic plumbing diagram showing the sample collecting apparatus of the present disclosure and specifically showing a purge valve adapted to be connected with a source of purge gas, a main valve which is a two position, three way valve, and further illustrating a dual needle system for filling a sample container through a septa and discharging surplus sample through a filter canister;

DETAIL DESCRIPTION AND PREFERRED EMBODIMENT

Figure 1:
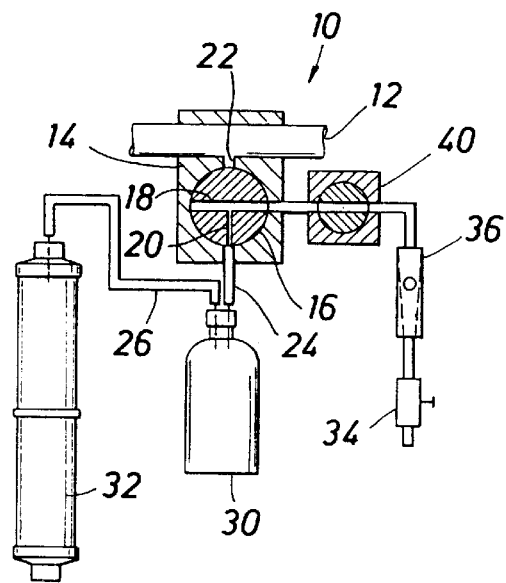

Attention is now directed to FIG. 1 of the drawing where the numeral 10 identifies the apparatus of the present disclosure. It is shown in greater detail in the mentioned co-pending applications which set forth details of construction of a dual needle system. In FIG. 1 of the drawings, the numeral 12 identifies a conduit which delivers the process fluid of interest. It can be at ambient temperature or can be at an elevated temperature, and the pressure can vary widely. If the pressure is quite high, a pressure regulator can be installed upstream of the equipment 10, but that has been omitted for sake of clarity. It is assumed that the pressure is reduced to a suitable working pressure for the equipment of the present disclosure. That typically is a pressure that is relatively low, perhaps about 100 psig. The conduit 12 thus delivers the fluid of interest, and again this fluid can be either a liquid or a gas. It can also be a fluid which typically tends to vaporize readily so that fugitive fumes may be formed.

As set forth in the above mentioned parent disclosure which is Ser. No. 882,033 and which was filed Jul. 13, 1992 and which is now issued as U.S. Pat. No. 5,345,828, it is not uncommon to provide a sample collection apparatus 10 which is constructed within a cabinet or a closed housing. It is not uncommon to make such a structure out of sheet metal. Indeed, it can be made as an explosion proof housing. The device of the present disclosure as shown in FIG. 1 is structurally mounted so that the conduit 12 is routed next to or into the cabinet. This can be conveniently done to deliver the process fluid of interest. Moreover, this cabinet supports the valves and lines shown in the drawings. As will be detailed, the conduit 12 connects with a valve 14 (described below) and a cooperative purge valve 40 adjacent to the valve 14.

The numeral 14 identifies the body of the structure which will be described as a valve body which encloses a valve element 16. The valve element 16 is a rotatable valve element which is provided with three ports. It is shown in the drawings switched between different positions, and each operative position is obtained by rotation through 90°. A suitable valve operator (not shown) can be incorporated to rotate the valve element by 90° steps. The valve typically can operate on 90° rotation typically provided by an operator. More importantly, the system utilizes the three port construction in a fashion which will be described in detail below.

There is a first passage 18 in the valve element 16. The passage 18 represents the main passage through the valve. Ideally, it is formed with the same passage diameter as connecting passages. A small purge passage 20 is also formed in the valve element 16 and connects to form the three-way connection. The passage 22 is aligned with and connects to the outlet line 24 through the valve element. The outlet 24 connects to a needle syringe. In similar fashion, there is another flow line 26 connected with another needle syringe. The two syringes are supported for insertion into the sample bottle 30 in the same fashion as discussed in the foregoing pending applications. The line 26 delivers overflow from the sample container 30 into the filter cartridge 32.

The sample container 30 is typically formed in a convenient size such as one half liter, one liter or perhaps 2 liters. It is provided with a narrow neck which is closed with a septum. The septais perforated by the two syringes which puncture the septaand extend into the interior. When the syringes are pulled from the septum, the septais self healing in that no leakage occurs. As further described in the mentioned disclosures, the sample container provides security and integrity for collecting and storing a sample so that the sample is readily available later. The sample container 30 is typically filled and then removed to another location for testing of the contents of the sample container. FIG. 1 further shows a control valve 34 which enables connection with a purge gas source. A flow meter 36 is also included to indicate that flow of the purge gas is occurring. Normally, the purge gas is nitrogen.

Figure 2:
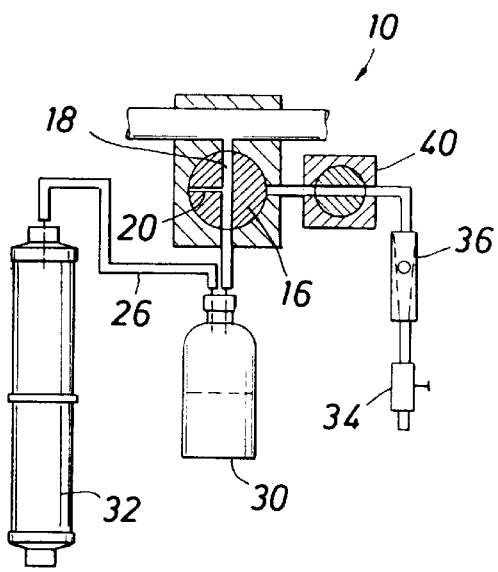
FIG. 2 is a view of the same structure shown in FIG. 1 where the main valve has been switched to another position.

Contrast FIG. 2 of the drawings with FIG. 1. There, the valve element 16 has been rotated to a different position. In FIG. 1 of the drawings, the purge gas is made available through the purge valve 40. This valve has two positions one being off and the other is on. More importantly, the two positions come into play in the entire operative cycle of this equipment. For the moment, FIGS. 1 and 2 both show the purge valve in the open position so that the purge gas is delivered. In FIG. 1 of the drawings, the purge gas is delivered through the valve element 16 where it flows through the small passage 20. It flows into the container 30 and through the filter 32. This flow of the purge gas clears the passages and assures that the sample container has only purge gas in it. This avoids any initial bias in the laboratory test that is run after capture of the sample.

FIG. 1 shows how the process fluid flows through the line 12 but no sample is taken to enable the purge gas to clear the sample container 30. FIG. 1 shows the operational positioning to get the equipment 10 ready for taking a sample. In FIG. 2 of the drawings, the valve element 16 has been rotated so that purge gas flow is interrupted. The valve element 16 has been rotated so that the sample of interest is delivered. In FIG. 2 of the drawings, this sample flow is delivered into the sample container 30. At this time, the purge gas flow is blocked. Blocking occurs at the three port valve. FIG. 2 shows how sample of interest is delivered for a timed interval. Again as noted, it may be necessary to interpose a flow regulator to control the flow. If the conduit 12 is delivering sample at a very elevated temperature and pressure, it is not uncommon to route the sample through a regulator to drop the pressure. In any case, the sample is delivered through the valve element 16 into the container 30 and surplus sample overflows from the container 30 into the filter 32.

Figure 3:
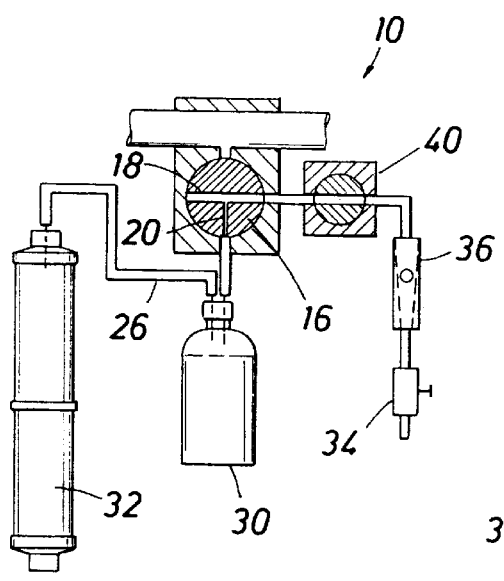
FIG. 3 is a view similar to FIG. 2 where the main valve has again been switched.

The equipment is operated to the position of FIG. 2 for only a short interval. It normally does not take a long time to capture the sample to fill the sample container 30. As will be understood, the sample container is installed on the two syringe needles which perforate the septa and open into the sample container 30 installed as a preliminary step by mounting the sample container as shown in FIG. 1 for gathering the sample as shown in FIG. 2. Once filling has been accomplished, the next step is to operate the valve element 16 to the rotated position which is shown in FIG. 3 of the drawings. In that sense, FIG. 3 of the drawings shows how the valves are switched back to the status achieved in FIG. 1. Particularly where the sample is a liquid, the sample container 30 is shown with a dotted line indicating partial filling in FIG. 2 and filling to a measured level in FIG. 3. This creates a dead space or volume above the liquid in the sample container 30. That space is purged by continuing flow of the purge gas as shown in FIG. 3 of the drawings. That is accomplished to assure that there is a cushion of inert gas in the container 30 above the liquid.

Going over FIG. 3 in detail, it will be observed that the purge gas forms a cushion or pillow over the liquid that is in the sample container 30. The purge gas can be directed through the sample container 30 for a selected duration. This assists in assuring that the lines of the equipment 10 are cleared of any remaining sample. As will be observed in FIG. 3, purge gas continues to flow through the purge valve 40 and is directed by the valve element 16 to flow through the port directing the purge gas into the sample container 30. This procedure is typically done for a short interval and then stopped. To the extent that any volatile constituents from the container 30 are carried out of the container, they are forced by the equipment 10 to flow through the cartridge 32 for filtration.

Figure 4:
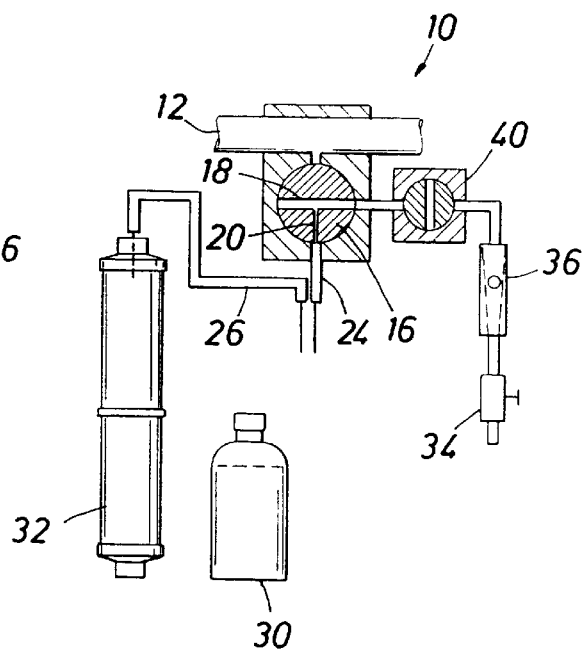
FIG. 4 is a view similar to FIGS. 1, 2 and 3 again showing the same apparatus after the sample container has been removed from the equipment for transfer to a laboratory and further showing that the purge valve has been closed to stop the flow of purge gas.

FIG. 4 of the drawings shows the equipment 10 after the sample container 30 has been disconnected. Disconnection is achieved by pulling the container downward. Valve blocking of flow is accomplished first and the bottle is disconnected and then the purge valve 40 is closed to block the purge gas flow to prevent waste of purge gas. At this point, the volatile product flowing in the line 12 is completely isolated from the apparatus 10 because the valve element 16 has been rotated to a position which assures that no further flow of sample material is received. In the arrangement shown in FIG. 4 of the drawings, when the equipment achieves the position illustrated, no more purge gas is permitted to flow, and the process materials continue to flow in the conduit 12 immediately adjacent to the equipment 10 but no sample is taken. There is no further flow into the container 32 because it has been disconnected from the syringes. Flow into the cartridge 32 is likewise interrupted at this time. In summary, this sets up the equipment 10 for the next cycle of use. The next cycle of use involves the replacement of the sample container 30 with a fresh container. The prior container 30 is filled through the sequence of steps shown in FIG. 1–4 and is removed to the sample laboratory for testing. A similar or duplicate sample container is immediately connected to the equipment 10 for the purpose of obtaining the next sample. The sampling sequence may vary, for instance, one sample may be obtained per day or perhaps one per hour. Other schedules can be used for obtaining samples.

The equipment 10 of this apparatus lends itself readily to a safe procedure. Samples can be taken time and again without venting any volatile constituents to the atmosphere. To the extent that there is any volatile fuming of a liquid sample, it is primarily captured in the sample container 30. If it flows out of the container 30, it is directed by the equipment 10 to flow into the filter cartridge 32. This operates the equipment in a safe mode and reduces, or even avoids the discharge of vaporized constituents to atmosphere.

One important factor in the use of this equipment is the fact that it is constructed so that there is a substantially fail safe sequence of operation. The sequence is initiated by the flow of the inert purge gas. It is terminated again by the flow of inert gas. This assures that the supply lines are first cleared of any atmosphere or filled with the purge gas. Every sample taken thereafter in accordance with this procedure is taken with precisely the same set of initial conditions.

The present procedure can be used indefinitely. It is desirable to use this procedure and practice in operation of the sampling system 10. More importantly, the sample taking system of this disclosure enables one to obtain a controlled sample. The controlled sample recovery system permits several sample containers accumulated over an interval of time to be delivered as collected or on a batch basis to a sample testing laboratory.

While the foregoing is directed to the preferred embodiment, the scope thereof is determined by the claims which follow:

What is claimed is:

1. A method of sampling a sample from a process fluid flow source comprising the steps of:
    (a) connecting a two position, three port valve between a fluid flow source to be tested for delivery of sample fluid flow into a sample receiving container;
    (b) operating said valve to a first position so that a purge fluid is directed through said valve from a valve controlled source as a preliminary step;
    (c) operating said valve to an alternate position so that a sample of specified size is delivered through said valve and is admitted into said sample container;
    (d) sequentially operating said valve so that said sample container is (1) first purged with a purge fluid and (2) then the sample is delivered into said container; and
    (e) after filling the container with sample, then (3) flowing purge fluid into said container.

2. The method of claim 1 wherein said valve is initially serially connected with a purge gas source and a serially connected purge gas valve to enable purge gas to flow through said valve into said sample container.

3. The method of claim 1 wherein said purge gas delivered in said preliminary step flows into said sample container and through a filter connected to said sample container.

4. The method of claim 1 wherein a surplus of sample overflows from said container into a filter connected to said container.

5. A method of removing a sample from a process fluid flow source comprising the steps of:
    (a) connecting in an alternating sequence a sample source and a purge gas source to an outlet;
    (b) delivering a first predetermined volume of a purge gas through a purge gas source blocking valve to said outlet;
    (c) then delivering a predetermined volume of a sample to be tested to said outlet; and
    (d) after filling a container to a specified volume of the sample, then delivering a second predetermined volume of a purge gas to said outlet to purge sample from the outlet so that any following tests are free of remnants of sample.

6. The method of claim 5 wherein said sample source and said purge gas source are alternatively connected to said outlet port through a valve element.

7. The method of claim 6 wherein said valve element is a two position, three port valve.

8. The method of claim 5 wherein said outlet is connected to a sample container allowing delivery of said sample to be collected in said sample container.

9. The method of claim 8 wherein said sample container is connected to a filter allowing said first volume of purge gas to fill said container and flow into said filter.

* * * * *